(12) United States Patent
Colbaugh et al.

(10) Patent No.: US 9,901,695 B2
(45) Date of Patent: Feb. 27, 2018

(54) RESPIRATORY INTERFACE APPARATUS

(75) Inventors: Michael Edward Colbaugh, Level Green, PA (US); Christopher Scott Lucci, Murrysville, PA (US)

(73) Assignee: Koninklijke Philips N.V., Eindhoven (NL)

( * ) Notice: Subject to any disclaimer, the term of this patent is extended or adjusted under 35 U.S.C. 154(b) by 982 days.

(21) Appl. No.: 13/703,698

(22) PCT Filed: May 18, 2011

(86) PCT No.: PCT/IB2011/025188
§ 371 (c)(1),
(2), (4) Date: Dec. 12, 2012

(87) PCT Pub. No.: WO2011/161561
PCT Pub. Date: Dec. 29, 2011

(65) Prior Publication Data
US 2013/0102916 A1     Apr. 25, 2013

Related U.S. Application Data

(60) Provisional application No. 61/357,200, filed on Jun. 22, 2010.

(51) Int. Cl.
*A61M 16/06* (2006.01)
*A61B 5/00* (2006.01)
(Continued)

(52) U.S. Cl.
CPC ............ *A61M 16/06* (2013.01); *A61B 5/085* (2013.01); *A61B 5/097* (2013.01); *A61B 5/4818* (2013.01);
(Continued)

(58) Field of Classification Search
CPC .. A61M 16/06; A61M 16/20; A61M 16/0057; A61M 16/0816; A61M 2230/432; A61M 2016/1025; A61M 2016/103; A61M 16/208; A61M 2202/0208;
(Continued)

(56) References Cited

U.S. PATENT DOCUMENTS 4,401,115 A   8/1983  Monnier
4,537,190 A   8/1985  Caillot et al.
(Continued)

FOREIGN PATENT DOCUMENTS

DE   29721766 U1   2/1998
EP    0774269 A1   5/1997
WO  2009127049 A1  10/2009

OTHER PUBLICATIONS

Thomas Penzel et al; "Effect of Sleep Position and Sleep Stage on the Collapsibility of the Upper Airways in Patients With Sleep Apnea", Journal of Sleep, vol. 24, No. 1, 2001, pp. 90-95.

*Primary Examiner* — (Jackie) Tan-Uyen T Ho
*Assistant Examiner* — Joseph D Boevker

(57) ABSTRACT

A respiratory interface apparatus (6) is provided that includes a patient contacting portion (21) structured to engage a face of the patient, a common chamber (30) fluidly coupled to the patient contacting portion (21), a first control chamber (26), a first flow regulating mechanism (32) provided between the first control chamber (26) and the common chamber (30), a second control chamber (28), and a second flow regulating mechanism (34) provided between the second control chamber (28) and the common chamber (30).

11 Claims, 2 Drawing Sheets

Figure 1:
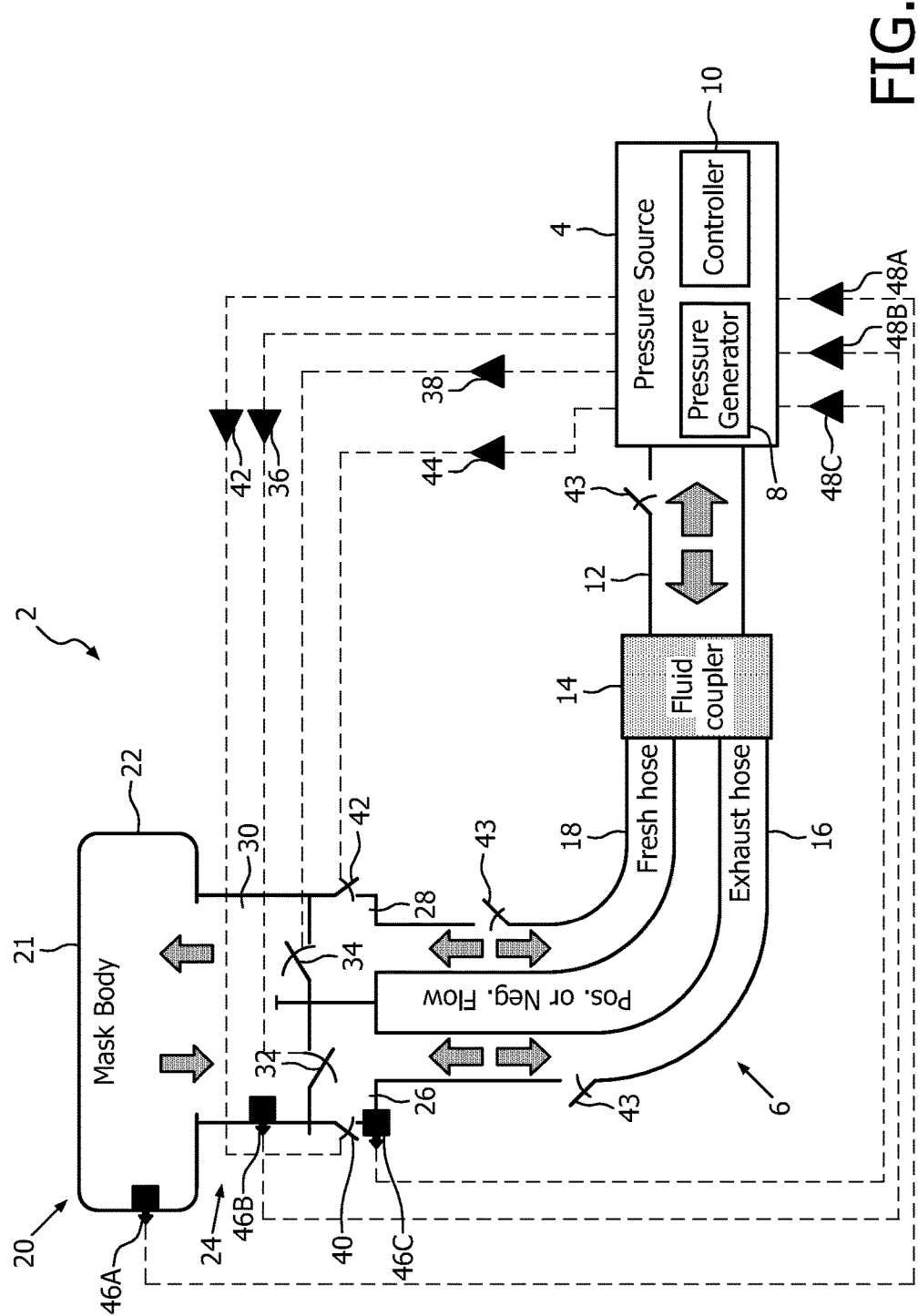

(51) Int. Cl.
*A61B 5/085* (2006.01)
*A61B 5/097* (2006.01)
*A61M 16/00* (2006.01)
*A61M 16/20* (2006.01)
*A61M 16/08* (2006.01)
*A61M 16/10* (2006.01)

(52) U.S. Cl.
CPC .... *A61M 16/0057* (2013.01); *A61M 16/0816* (2013.01); *A61M 16/0833* (2014.02); *A61M 16/20* (2013.01); *A61M 16/208* (2013.01); A61M 2016/0027 (2013.01); A61M 2016/0036 (2013.01); A61M 2016/0042 (2013.01); *A61M 2016/103* (2013.01); A61M 2016/1025 (2013.01); A61M 2202/0208 (2013.01); A61M 2202/0275 (2013.01); A61M 2230/432 (2013.01); A61M 2230/435 (2013.01)

(58) Field of Classification Search
CPC ....... A61B 5/4818; A61B 5/097; A61B 5/085
USPC ........... 128/203.12, 203.14, 205.16, 204.18, 128/204.26, 205.1, 205.11, 205.14, 128/205.15; 600/431, 529, 549
See application file for complete search history.

(56) References Cited

U.S. PATENT DOCUMENTS

| | | | | |
|---|---|---|---|---|
| 4,622,976 A * | 11/1986 | Timpe | ................ | A61B 5/0275 128/203.14 |
| 4,781,184 A * | 11/1988 | Fife | ................ | 128/205.12 |
| 4,838,257 A * | 6/1989 | Hatch | ................ | A61M 16/00 128/204.18 |
| 4,903,693 A * | 2/1990 | Yasue | ................ | A61M 15/02 128/203.12 |
| 5,694,929 A * | 12/1997 | Christopher | ...... | A61M 16/0488 128/205.25 |
| 6,253,764 B1 | 7/2001 | Calluaud | | |
| 2001/0020471 A1 | 9/2001 | Kitten | | |
| 2002/0005197 A1* | 1/2002 | DeVries | .............. | A61M 16/125 128/204.21 |
| 2002/0020410 A1* | 2/2002 | Rydin | ............... | A61M 16/0051 128/200.24 |
| 2002/0023646 A1 | 2/2002 | Heesch | | |
| 2002/0029004 A1* | 3/2002 | Starr | ................ | A61B 5/087 600/538 |
| 2005/0284476 A1 | 12/2005 | Blanch et al. | | |
| 2007/0062531 A1* | 3/2007 | Fisher | ................ | A61B 5/083 128/204.23 |
| 2008/0060646 A1* | 3/2008 | Isaza | ................ | A61M 16/0468 128/204.21 |
| 2008/0202524 A1 | 8/2008 | Mitton et al. | | |
| 2008/0264412 A1* | 10/2008 | Meyer | ............... | A61M 15/0086 128/200.22 |
| 2009/0082639 A1 | 3/2009 | Pittman et al. | | |
| 2010/0101578 A1* | 4/2010 | Cha | ................ | A61B 5/087 128/205.24 |
| 2011/0208539 A1* | 8/2011 | Lynn | ................ | A61B 5/087 705/2 |
| 2012/0111331 A1* | 5/2012 | Witt | ................ | A61M 16/0666 128/205.25 |

\* cited by examiner

RESPIRATORY INTERFACE APPARATUS

The present invention relates to respiratory pressure testing (e.g., diagnostic testing) and therapy including use of such testing and therapy in diagnosing and treating sleep disordered breathing, and in particular relates to a system and method for effectively controlling exhaled gases, such as $CO_2$, and/or re-breathing of exhaled gases, such as $CO_2$, during respiratory pressure testing and therapy.

A number of methods and tests for diagnosing sleep disordered breathing conditions involving some extent of respiratory failure, such as obstructive sleep apnea and central apnea, have been developed. One of the most popular methods involves probing the severity and nature of the respiratory failure using a mask and a flow generating device that is set to deliver multiple varying breathing gas pressures to the airway of the patient through the mask. In this method, the breathing gas pressures that are delivered to the patient range from positive to negative with respect to atmospheric pressure, and the mask part of the system is sealed from the ambient environment.

In some testing sequences, the flow of breathing gas is set to zero or very near zero, and the patient is essentially breathing under his or her own power. At zero flow, exhaust gases from the patient can build $CO_2$ in the mask and the hose or other conduit connecting the mask to the flow generating device (collectively referred to as the breathing circuit). Such $CO_2$ build-up within the breathing circuit can be problematic as it may effect some of the measurements/readings that are taken and often makes the mask and system uncomfortable for the patient. This is especially challenging when the pressure source flow to or from the mask is close to zero.

As noted above, the described patient therapy/test systems sometimes require negative pressures, which means negative airflow draws on the patient's breathing to aid exhalation or resist inhalation effort. Controlling exhaled $CO_2$ in such a situation is often particularly challenging. In addition, there are testing schemes where it is desired to reduce the amount of resistance to exhale or inhale flow, or the amount of pressure from the pressure source, for patient comfort or other some other function. In such schemes, it is difficult for the pressure source to react adequately or to relieve mask pressure at various times in the respiratory cycle while flushing the line of undesired $CO_2$ or other exhaled gases.

One particular area where exhaled gases such as $CO_2$ can be a problem is in the determination of sleep phenotyping parameters (commonly referred to as sleep phenotyping). Sleep phenotyping parameters comprise metrics that quantify aspects of the physiology and/or physiological performance of an individual that characterize a sleep phenotype of the individual. The sleep phenotype of an individual describes the predisposition of that individual (e.g., due to physiological characteristics of the individual) to one or more sleep disorders (e.g., obstructive sleep apnea, Cheyne-Stokes breathing, restless legs syndrome, etc.). Examples of sleep phenotyping parameters include critical pharyngeal closing pressure, upper airway vibration characteristics, upper airway muscle responsiveness, arousal threshold, and ventilatory control feedback loop gain. United States Patent Application Publication No. 2009/0082639, owned by the assignee of the present invention and entitled "Automatic Sleep Phenotyping", the disclosure of which is incorporated herein by reference, describes a system that determines one or more sleep phenotyping parameters of a subject by providing a stimulus to the subject when a trigger condition relating to the current sleep stage of the subject has been met, wherein the response of the subject to the stimulus enables information related to the one or more sleep phenotyping parameters to be determined. In one embodiment of such a system, the stimulus that is provided to the subject is a flow of pressurized gas delivered to the airway of the subject. In such a system, the presence of exhaled gases such as $CO_2$ in the breathing circuit can adversely effect the parameters being measured.

There is thus a need for a system and method for effectively controlling exhaled $CO_2$ and/or $CO_2$ re-breathing during respiratory pressure testing (e.g., diagnostic testing) and therapy including sleep disordered breathing testing situations.

In one embodiment, a respiratory interface apparatus is provided that includes a patient contacting portion structured to engage a face of the patient, a common chamber fluidly coupled to the patient contacting portion, a first control chamber, a first flow regulating mechanism provided between the first control chamber and the common chamber, a second control chamber, and a second flow regulating mechanism provided between the second control chamber and the common chamber.

In another embodiment, a method controlling a flow of one or more exhaled gases during respiratory pressure therapy or testing is provided that includes attaching a respiratory interface apparatus to a head of a patient, the respiratory interface apparatus having a contacting portion structured to engage a face of the patient, a common chamber fluidly coupled to the patient contacting portion, a first control chamber, and a second control chamber. The method also includes, during an expiratory phase of the patient's respiratory cycle, permitting fluid flow from the common chamber to the first control chamber and restricting fluid flow from the common chamber to the second control chamber to prevent a first predetermined amount of a patient exhaust flow from entering the second control chamber, and during an inspiratory phase of the patient's respiratory cycle, permitting fluid flow from the second control chamber to the common chamber and restricting fluid flow from the first control chamber to the common chamber to prevent a predetermined amount of at least one of the one or more exhaled gases from flowing into the common chamber from the first control chamber.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Figure 2:
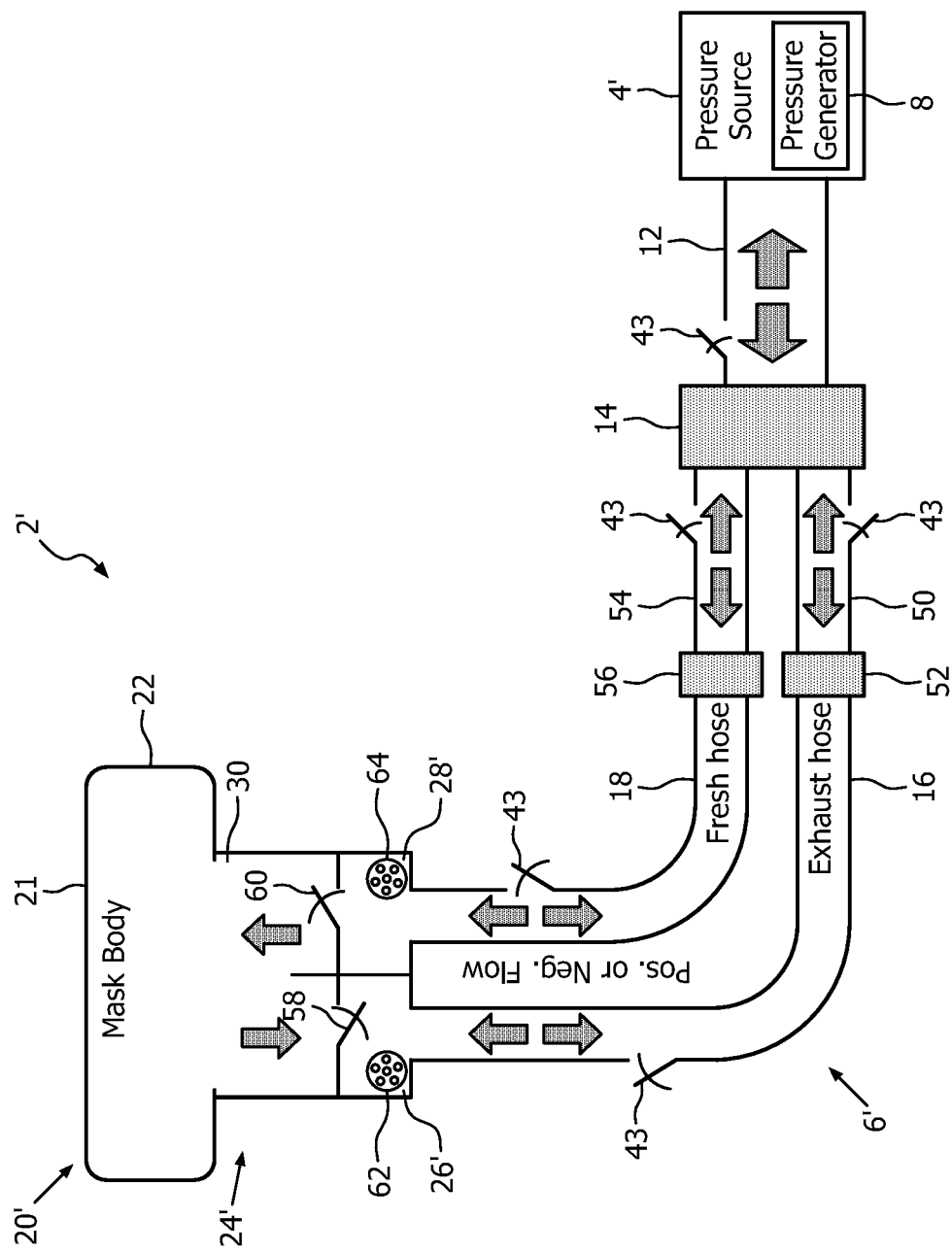

FIG. 1 is a schematic diagram of system for controlling the flow of one or more exhaled gases, such as $CO_2$, and controlling re-breathing of one or more exhaled gases, such as $CO_2$, during respiratory pressure testing or therapy according to one exemplary embodiment of the present invention; and FIG. 2 is a schematic diagram of system for controlling the flow of one or more exhaled gases, such as $CO_2$, and controlling re-breathing of one or more exhaled gases, such as $CO_2$, during respiratory pressure testing or therapy according to an alternative exemplary embodiment of the present invention.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed, herein, the statement that two or more parts or components are "coupled" together shall mean that the parts are joined or operate together either directly or through one or more intermediate parts or components.

As employed herein, the statement that two or more parts or components "engage" one another shall mean that the parts exert a force against one another either directly or through one or more intermediate parts or components.

As employed herein, the term "number" shall mean one or an integer greater than one (i.e., a plurality).

FIG. 1 is a schematic diagram of system 2 for controlling the flow of exhaled gases, such as $CO_2$, and in particular controlling re-breathing of exhaled gases, such as $CO_2$, during respiratory pressure testing or therapy according to one exemplary embodiment of the present invention. System 2 includes pressure source 4 operatively coupled to patent interface apparatus 6. Pressure source 4 in the illustrated embodiment includes pressure generator 8 and controller 10. Pressure generator 8 is configured to generate a pressurized flow of breathable gas for delivery to the airway of the patient via patent interface apparatus 6. One or more parameters of the pressurized flow of breathable gas generated by pressure generator 8 may be controlled by pressure generator 8. For example, pressure generator 8 may control one or more of the pressure, the flow rate, the composition, and/or other parameters of the pressurized flow of breathable gas. In one embodiment, pressure generator 8 includes a gas source and one or more components that control the flow and/or pressure of a pressurized flow of gas generated from the gas within the gas source. The gas source may include any supply (or supplies) of breathing gas, such as, for example, ambient atmosphere, a tank of pressurized gas, a wall gas source, and/or other bodies of breathable gas. The breathing gas from the gas source can be any breathable gas, such as air, oxygen, an oxygen mixture, a mixture of a breathing gas and a medication, which can be in gaseous form (e.g., nitric oxide, nebulized, etc.), and/or other breathable gases. The one or more components that control one or more parameters of the pressurized flow of breathable gas may include one or more of a valve, a blower, a piston, a bellows, and/or other mechanisms for controlling one or more parameters of the pressurized flow of breathable gas. Controller 10 may be, for example and without limitation, a microprocessor or a microcontroller. The function of controller 10 in the illustrated embodiment is described elsewhere herein.

Patent interface apparatus 6 in the illustrated embodiment also includes conduit 12, wherein a first end of conduit 12 is fluidly coupled to an output of pressure source 4, and in particular the output of pressure generator 8. A second end of conduit 12 is fluidly coupled to an input of fluid coupler 14. Fluid coupler 14 transforms a single input fluid path into two output fluid paths. A first one of those output fluid paths is fluidly coupled to exhaust hose/conduit 16, and a second one of those output fluid paths is fluidly coupled to fresh hose/conduit 18.

Patent interface apparatus 6 further includes patient interface assembly 20. Patient interface assembly 20 includes mask body 22 that is in fluid communication with flow control assembly 24, the details of which are described below. Mask body 22 facilitates the delivery of the flow of breathing gas generated by pressure source 4 to the airway of a patient, and may be, without limitation, a nasal mask, a nasal/oral mask, or a full face mask. In an exemplary embodiment, mask body 22 includes a patient contacting portion 21 (e.g., a cushion) coupled to a frame or shell. The patient contacting portion 21 is made of a soft, flexible material, such as, without limitation, silicone, an appropriately soft thermoplastic elastomer, a closed cell foam, or any combination of such materials. In addition, the frame or shell is made of a rigid or semi-rigid material such as, without limitation, polycarbonate or reinforced silicone. An opening in the frame or shell is provided in order to enable mask body 22 to be fluidly coupled to flow control assembly 24.

Flow control assembly 24 includes exhaust side control chamber 26 that is fluidly coupled to exhaust hose/conduit 16 and fresh side control chamber 28 that is fluidly coupled to fresh hose/conduit 18. Flow control assembly 24 further includes common chamber 30 that is fluidly coupled to mask body 22. In the illustrated embodiment, exhaust side control chamber 26 includes active exhaust side flow control valve 32 and fresh side control chamber 28 includes active fresh side flow control valve 34. In the illustrated embodiment, exhaust side flow control valve 32 and fresh side flow control valve 34 may be any type of suitable, electromechanically operated valve. Exhaust side flow control valve 32 is actuated by driver/actuator 36 under the control of processor 10, and similarly fresh side flow control valve 34 is actuated by driver/actuator 38 under the control of processor 10. Exhaust side control chamber 26 and fresh side control chamber 28 may each be selectively placed in fluid communication with common chamber 30 through selective actuation of exhaust side flow control valve 32 and fresh side flow control valve 34, respectively.

In addition, in the illustrated embodiment, exhaust side control chamber 26 includes active exhaust side venting valve 40 and fresh side control chamber 28 includes active fresh side venting valve 42 which may be used to selectively vent exhaust side control chamber 26 and fresh side control chamber 28 to atmosphere. In the illustrated embodiment, exhaust side venting valve 40 and fresh side venting valve 42 may be any type of suitable, electromechanically operated valve. Exhaust side venting valve 40 is actuated by driver/actuator 44 under the control of processor 10, and similarly fresh side venting valve 42 is actuated by driver/actuator 46 under the control of processor 10.

As seen in FIG. 1, patent interface apparatus 6 also includes a number of sensors for sensing parameters such as one or more of pressure, $CO_2$ level, $O_2$ level or flow rate within various parts of patent interface apparatus 6. In the illustrated embodiment, patent interface apparatus 6 includes first parameter sensor 46A provided within mask body 22, second parameter sensor 46B provided within common chamber 30, and third parameter sensor 46C provided within exhaust side control chamber 26. Information gathered by first, second and third parameter sensors 46A, 46B and 46C is provided to processor 10 through sensor acquisition interfaces 48A, 48B, 48C. Furthermore, pressure, flow, $CO_2$ and/or $O_2$ sensors may be employed in any section of the air paths of the system 2, in any valve/port described above, and/or in the environment surrounding system 2.

System 2 as described herein may be used any time a closed pressurized system is needed for respiratory testing, therapy, or other respiratory purpose. For example, system 2 may be used for testing purposes in order to diagnose sleep disordered breathing in a patient. Alternatively, system 2 may be used to provide pressure support therapy to treat a sleep disordered breathing condition of a patient. In any such uses, pressure of various levels (positive and/or negative) is generated by pressure source 4 and is provided to the airway of the patient during one or more portions of or all of the patient's respiratory cycle. As will be appreciated by those of skill in the art, the particulars of such pressure levels will depend on and be dictated by the needs of the particular application. Regardless of such particulars, the present invention provides a mechanism for effectively controlling the flow of exhaled gases, such as $CO_2$, and controlling re-breathing of exhaled gases, such as $CO_2$, when the pressure levels are provided to the patient.

Operation of system 2 according to one exemplary embodiment of the invention will now be described. During the expiratory phase of the patient's respiratory cycle: (i) exhaust side flow control valve 32 is partially or fully opened to enable exhaust flow from the patient to be vented to the exhaust hose/conduit 16 and out valve 40 and/or 43 and back to the pressure source 4 if the pressure of the pressure source output is less than that in the exhaust hose 16, and (ii) fresh side flow control valve 34 is fully or partially closed to prevent an unwanted amount (e.g. from zero up to some permissible threshold level) of one or more gases, such as $CO_2$, (from the patient exhaust flow) from passing down through fresh hose/conduit 18. During the inspiratory phase of the patient's respiratory cycle: (i) exhaust side flow control valve 32 is fully or partially closed to prevent an unwanted amount (e.g. from zero up to some permissible threshold level) of one or more gases, such as $CO_2$, from flowing into common chamber 30 and mask body 22, and (ii) fresh side flow control valve 34 is partially or fully opened to enable fresh gas (provided at least in part by pressure source 4) to be provided to the patient through common chamber 30 and mask body 22. It should be understood that the fresh gas supply may or may not include some negative flow bias, which may be desired in the therapy or testing use of system 2.

Furthermore, exhaust side venting valve 40 may be partially or fully opened during the expiratory phase of the patient's respiratory cycle to relieve pressure within mask body 22 or flow control assembly 24 when the pressure and/or flow and/or $CO_2$ (or some other exhaled gas) level and/or $O_2$ level in one or more of mask body 22, common chamber 30 or exhaust side control chamber 26 exceeds a predetermined threshold as measured by one or more of the parameter sensors 46A, 46b, 46C. In addition, fresh side venting valve 42 may be partially or fully opened during the inspiratory phase of the patient's respiratory cycle to supplement the gas flow from pressure source 4 with supplemental flow from the ambient atmosphere. This may be important if the fresh hose/conduit 18 is too small or pressure source 4 is limited in providing adequate flow at a peak portion during the inspiratory phase.

In addition, additional active or passive valves 43 may be provided in any or all of exhaust hose/conduit 16, fresh hose/conduit 18 or conduit 12. When such valves 43 are provided, exhaust side venting valve 40 and/or fresh side venting valve 42 may be partially or fully opened to enable fresh air to flush the exhaust hose/conduit 16, fresh hose/conduit 18 and or conduit 12, with the flushing air flow being vented to atmosphere through flow provided in any or all of exhaust hose/conduit 16, fresh hose/conduit 18 or conduit 12. These additional valves 43 may also be used to vent pressure or exhaust gas from system 2.

In addition, one or more of exhaust side flow control valve 32, fresh side flow control valve 34, exhaust side venting valve 40 and fresh side venting valve 42 may be controlled to enable a predetermined amount of gases, such as $CO_2$, generated and exhaled by the patient, to be trapped in one or both of the air paths defined by exhaust hose/conduit 16 and fresh hose/conduit 18 and be re-breathed by the patient.

Furthermore, controller 10 may be structured to interface to other equipment and/or operators, and/or may include a memory to record information, a power supply, and/or other common features of known electronic device control systems.

According to an alternative embodiment, control of exhaust side flow control valve 32, fresh side flow control valve 34, exhaust side venting valve 40 and fresh side venting valve 42 is entirely provided by a living operator. Sensors (as described above), a scheme for displaying information (such as sensor outputs) for the living operator, and means for enabling the operator to control the actuators 36, 38, 42, 44 are provided in this configuration. Semi-automated control means may also be provided to assist the operator.

FIG. 2 is a schematic diagram of system 2' for controlling the flow of one or more exhaled gases, such as $CO_2$, re-breathing of one or more exhaled gases, such as $CO_2$, during respiratory pressure testing or therapy according to an alternative exemplary embodiment of the present invention. System 2' is similar to system 2 shown in FIG. 1 and described above, and like components are labeled with like reference characters. However, system 2' differs from system 2 in a number of ways as described below.

System 2' includes pressure source 4' operatively coupled to patent interface apparatus 6'. Pressure source 4' in the illustrated embodiment includes pressure generator 8 as described elsewhere herein, but does not include a separate controller 10 (as is known in the art, pressure generator 8 may include its own processor for controlling the delivery of breathing gas at the desired pressure levels).

Patent interface apparatus 6' in the illustrated embodiment includes conduit 12 coupled to an input of fluid coupler 14 as described elsewhere herein in connection with system 2. However, patent interface apparatus 6' of system 2' further includes first intermediate conduit 50 coupled to fluid coupler 52 and second intermediate conduit 54 coupled to fluid coupler 56. As seen in FIG. 2, first and second intermediate conduits 50, 54 are coupled to the outputs of fluid coupler 14. As also seen in FIG. 2, fluid coupler 52 is fluidly coupled to exhaust hose/conduit 16, fluid coupler 56 is fluidly coupled to fresh hose/conduit 18. In the illustrated embodiment, first and second intermediate conduits 50, 54 having a larger diameter than each of exhaust hose/conduit 16 and fresh hose/conduit 18 (e.g., first and second intermediate conduits 50, 54 may each be standard 22 mm hose and exhaust hose/conduit 16 and fresh hose/conduit 18 may each be 15 mm hoses. The smaller diameter of exhaust hose/conduit 16 and fresh hose/conduit 18 provides greater comfort to the patient during sleep, as long as the resistance to flow does not become high enough to prevent the pressure source 4' from providing the flow and pressure required, and as long as the resistance does not become disturbing to the subject. Such a configuration may also be used in the embodiment of FIG. 1.

Patent interface apparatus 6' further includes patient interface assembly 20'. Patient interface assembly 20' includes mask body 22 as described elsewhere herein in connection with FIG. 1 that is in fluid communication with flow control assembly 24', the details of which are described below.

Flow control assembly 24' includes exhaust side control chamber 26' that is fluidly coupled to exhaust hose/conduit 16 and fresh side control chamber 28' that is fluidly coupled to fresh hose/conduit 18. Flow control assembly 24' further includes common chamber 30 that is fluidly coupled to mask body 22. In the illustrated embodiment, exhaust side control chamber 26' includes exhaust side flow control valve 58 in the form of a one-way passive valve, and fresh side control chamber 28' includes fresh side flow control valve 60 also in the form of a one-way passive valve. Exhaust side flow control valve 58 and fresh side flow control valve 60 may be any type of suitable, passive flow regulating/restricting valve, such as, without limitation, a pressure actuated duckbill valve. Alternatively, exhaust side flow control valve 58 and fresh side flow control valve 60 may be any type of suitable, non-valve type passive flow regulating/restricting, such as, without limitation, a one way valve such as a flapper valve, parachute valve, one-direction fan or turbine.

In addition, exhaust side control chamber 26' includes passive flow regulating/restricting mechanism 62 and fresh side control chamber 28' includes passive regulating/restricting mechanism 64 which may be used to vent exhaust side control chamber 26' and fresh side control chamber 28' to atmosphere. In the illustrated embodiment, flow regulating/restricting mechanisms 62, 64 are each a fixed leak/fixed resistance port comprising a disk shaped member having a plurality of orifices, although other suitable passive flow regulating/restricting mechanisms such as, without limitation, a passive one-way valve, may also be used.

In the illustrated embodiment, during the expiratory phase of the patient's respiratory cycle: (i) exhaust side flow control valve 58 is, in response to patient exhalation flow, caused to be opened to enable exhaust flow from the patient to be vented to the exhaust hose/conduit 16 out valve 40 and/or 43 and back to the pressure source 4 if the pressure of the pressure source output is less than that in the exhaust hose 16, and (ii) fresh side flow control valve 60 is closed (e.g., biased closed) to prevent one or more gases, such as $CO_2$, (from the patient exhaust flow) from passing down through fresh hose/conduit 18. During the inspiratory phase of the patient's respiratory cycle: (i) exhaust side flow control valve 58 is closed (e.g., biased closed) to prevent one or more gases, such as $CO_2$, from flowing into common chamber 30 and mask body 22, and (ii) fresh side flow control valve 60 is caused to be opened to enable fresh gas (provided at least in part by pressure source 4') to be provided to the patient through common chamber 30 and mask body 22.

Furthermore, passive flow regulating/restricting mechanism 62 may, during the expiratory phase of the patient's respiratory cycle, relieve pressure within mask body 22 or flow control assembly 24. In addition, passive flow regulating/restricting mechanism 64 may, during the inspiratory phase of the patient's respiratory cycle, supplement the gas flow from pressure source 4' with supplemental flow from the ambient atmosphere.

In other alternative exemplary embodiments, system 2 or system 2' may be modified such that the flow path including exhaust hose/conduit 16 and the flow path including fresh hose/conduit 18 each have a separate pressure source 4 or 4' or such that one or both of such flow paths are vented directly to atmospheric pressure (rather than being coupled to pressure source 4 or 4'). In still another alternative exemplary embodiment, system 2 or system 2' may be configured without exhaust hose/conduit 16 and fresh hose/conduit 18, with the associated hose ports being blocked-off. With this configuration, atmospheric pressure is the reference and limited diagnostics can be performed, using the flow control valves 32, 34, 58, 60 and resistance pressure (both positive and negative) generated by control of the flow resistance of valves 40, 42 and flow regulating/restricting mechanisms 62, 64. In connection with such a variation of system 2, controller 10 may be separate from patient interface assembly 20 or 20' but in communication with same, or integrated into patient interface assembly 20 or 20', such as in the mask body 22.

According to further alternative embodiments, some or all of the valves, ports, and sensors described above may be integrated into a mask body such as mask body 22 as is viable within the requirements of the testing/therapy scheme. It should also be understood that the valves described herein may actually be multiple valve arrangements, or may be combinations of passive and actively controlled valves.

As noted elsewhere herein, the present invention may be employed in multiple situations where a closed pressurized system is needed for respiratory testing, therapy, or other respiratory purpose. For example, and without limitation, the present invention may be used to implement an interface system for a Critical Pressure (Pcrit) respiratory diagnostic system, to implement an interface system for the provision of respiratory therapy (especially with low flow rate), to implement an interface system for the provision of ventilatory therapy or assistance (especially with low flow rate), as a self-contained ventilatory therapy mask, or as a self-contained Pcrit diagnostic system.

In one specific, non-limiting example, the present invention may be employed during automatic sleep phenotyping to control the flow of one or more exhaled gases, such as $CO_2$. More specifically, as stated elsewhere herein, United States Patent Application Publication No. 2009/0082639, the disclosure of which is incorporated herein by reference, describes a system that determines one or more sleep phenotyping parameters of a subject. In one embodiment, the system includes a sleep sensor, a stimulus generator, and a processor. The sleep sensor generates signals that convey information related to the physiological functions that indicate the sleep stage of the subject. The stimulus generator provides a stimulus to the subject that enables information related to the sleep phenotyping parameters to be determined. The processor receives the signals generated by the sleep sensor and is in operative communication with the stimulus generator. The processor (i) determines, based on the signals received from the sleep sensor, whether a trigger condition related to the current sleep stage of the subject is satisfied, (ii) controls the stimulus generator to provide the stimulus to the subject if the trigger condition is satisfied, and (iii) quantifies the response of the subject to the stimulus to enable information related to one or more sleep phenotyping parameters of the subject to be determined. In one particular embodiment, the stimulus generator comprises a device that provides a flow of pressurized gas to the airway of a subject to support the airway during sleep (e.g., a Positive Airway Pressure device ("PAP device")). Provision of such a stimulus to the subject may include reducing the pressure of the flow of gas to levels at which the subject is susceptible to respiratory challenges (e.g., apneas, airway obstructions, etc.). Thus, in one exemplary embodiment, patent interface apparatus 6 or patent interface apparatus 6' may be employed in a sleep phenotyping system, such as, without limitation, the sleep phenotyping just described, to control the flow of one or more exhaled gases, such as $CO_2$. In another exemplary embodiment, system 2 or 2' discussed herein may be modified/configured to implement an automatic sleep phenotyping system as described in, for example, United States Patent Application Publication No. 2009/0082639, by providing the necessary sleep sensor or sensors and programming the controller thereof to operate as describe in United States Patent Application Publication No. 2009/008263. By controlling the flow of one or more exhaled gases, such as $CO_2$, the adverse effect that such exhaled gases may have on the measured parameters may be limited.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A respiratory interface apparatus, comprising:
    a patient contacting portion structured to engage a face of a patient;
    a common chamber fluidly coupled to the patient contacting portion;
    a first control chamber;
    a first flow regulating mechanism provided between the first control chamber and the common chamber;
    a second control chamber;
    a second flow regulating mechanism provided between the second control chamber and the common chamber;
    a first conduit;
    a second conduit; and
    a pressure source including a controller,
    wherein the first flow regulating mechanism is a first active valve controlled by the controller and is structured to selectively fluidly couple the first control chamber to the common chamber, and wherein the second flow regulating mechanism is a second active valve controlled by the controller and is structured to selectively fluidly couple the second control chamber to the common chamber,
    wherein the controller is structured to actuate the first active valve in a first predetermined manner and actuate the second active valve in a second predetermined manner during an expiratory phase of the patient's respiratory cycle, wherein the controller is structured to actuate the first active valve in a third predetermined manner and actuate the second active valve in a fourth predetermined manner during an inspiratory phase of the patient's respiratory cycle,
    wherein the actuation in the first predetermined manner opens the first active valve, wherein the actuation in the second predetermined manner closes the second active valve, wherein the actuation in the third predetermined manner closes the first active valve, and wherein the actuation in the fourth predetermined manner opens the second active valve, and
    wherein the first control chamber further includes a third flow regulating mechanism to selectively or constantly couple the first control chamber to atmosphere and the second control chamber further includes a fourth flow regulating mechanism structured to selectively or constantly couple the second control chamber to atmosphere,
    wherein the first conduit is fluidly coupled to the first control chamber and the second conduit is fluidly coupled to the second control chamber, and
    wherein the first control chamber is fluidly coupled between the first conduit and the common chamber and is structured to receive breathing gas from the pressure source via the first conduit and the second control chamber is fluidly coupled between the second conduit and the common chamber and is structured to receive breathing gas from the pressure source via the second conduit.

2. The respiratory interface apparatus according to claim 1, wherein the patient contacting portion is part of a mask body, and wherein the common chamber, the first control chamber and the second control chamber are coupled to the mask body and together form a patent interface assembly.

3. The respiratory interface apparatus according to claim 1, wherein the pressure source is structured to generate a flow of breathing gas, the first conduit and the second conduit being fluidly coupled to the pressure source.

4. The respiratory interface apparatus according to claim 3, wherein the pressure source includes a pressure generator.

5. The respiratory interface apparatus according to claim 4, wherein the controller is structured to actuate the first active valve in the first predetermined manner and actuate the second active valve in the second predetermined manner during the expiratory phase of the patient's respiratory cycle to enable exhaust flow from the patient to be vented to the first conduit and to prevent a predetermined amount of the patient exhaust flow from entering the second conduit, and wherein the controller is structured to actuate the first active valve in the third predetermined manner and actuate the second active valve in the fourth predetermined manner during the inspiratory phase of the patient's respiratory cycle to prevent a predetermined amount of $CO_2$ from flowing into the common chamber from the first conduit and to enable gas provided by the pressure source to flow into the common chamber from the second conduit.

6. The respiratory interface apparatus according to claim 1, wherein the third flow regulating mechanism is a third active valve controlled by the controller and the fourth flow regulating mechanism is a fourth active valve controlled by the controller, wherein the controller is structured to actuate the third active valve in a fifth predetermined manner and actuate the fourth active valve in a sixth predetermined manner during the expiratory phase of the patient's respiratory cycle, and wherein the controller is structured to actuate the third active valve in a seventh predetermined manner and actuate the fourth active valve in an eighth predetermined manner during the inspiratory phase of the patient's respiratory cycle.

7. The respiratory interface apparatus according to claim 6, wherein the respiratory interface apparatus includes one or more sensors operatively coupled to the controller, and wherein the controller controls one or more of the first, second, third and fourth active valves based on an output of the one or more sensors.

8. The respiratory interface apparatus according to claim 7, wherein the one or more sensors sense one or more of pressure, $CO_2$ level, $O_2$ level and flow rate.

9. The respiratory interface apparatus according to claim 3, wherein the third flow regulating mechanism and the fourth flow regulating mechanism are passive.

10. The respiratory interface apparatus according to claim 9, wherein the third flow regulating mechanism and the fourth flow regulating mechanism are each one of a one-way passive valve, a fixed leak port, and a fixed resistance port.

11. A system of enabling determination of one or more sleep phenotyping parameters of a subject including the respiratory interface apparatus according to claim 1.

* * * * *